US008922377B2

(12) United States Patent
Carnes

(10) Patent No.: US 8,922,377 B2
(45) Date of Patent: Dec. 30, 2014

(54) SYSTEM, METHOD, AND SOFTWARE FOR AUTOMATING COMPLEX ALERTS

(75) Inventor: Tony C. Carnes, Gainesville, FL (US)

(73) Assignee: Covidien LP, Mansfield, MA (US)

( * ) Notice: Subject to any disclaimer, the term of this patent is extended or adjusted under 35 U.S.C. 154(b) by 168 days.

(21) Appl. No.: 13/537,633

(22) Filed: Jun. 29, 2012

(65) Prior Publication Data
US 2014/0002265 A1   Jan. 2, 2014

(51) Int. Cl.
G08B 23/00   (2006.01)
(52) U.S. Cl.
USPC ............... 340/573.1; 340/539.12; 600/301; 706/47
(58) Field of Classification Search
USPC ............ 340/573.1, 539.1, 539.11, 539.12, 340/539.13; 600/310, 309, 300, 301; 706/45, 47, 52, 62
See application file for complete search history.

(56) References Cited

U.S. PATENT DOCUMENTS

| 7,978,062 | B2 * | 7/2011 | LaLonde et al. ......... 340/539.11 |
| 8,175,895 | B2 | 5/2012 | Rosenfeld et al. |
| 2007/0219830 | A1 * | 9/2007 | Warner et al. ................. 705/3 |
| 2008/0162254 | A1 * | 7/2008 | Herger et al. ................. 705/9 |
| 2009/0278696 | A1 | 11/2009 | Lindh et al. |
| 2011/0137852 | A1 | 6/2011 | Gajic et al. |
| 2011/0202490 | A1 | 8/2011 | Gawlick |

OTHER PUBLICATIONS

International Search Report and Written Opinion for PCT Application No. PCT/US2013/046217, dated Sep. 12, 2013, 6 pages.

* cited by examiner

*Primary Examiner* — Anh V La
(74) *Attorney, Agent, or Firm* — Carter DeLuca Farrell & Schmidt LLP

(57) ABSTRACT

A method for automating complex alerts includes receiving, at a complex alert interface, first parameters from at least one medical device and a first comparison operator. The first parameters and the first comparison operator are indicative of a first condition. The method further includes receiving, at the complex alert interface, second parameters from the at least one medical device and a second comparison operator. The second parameters and the second comparison operator are indicative of a second condition. The method further includes generating, at the complex alert interface, a complex alert expression based on a mathematical aggregate of the first condition and the second condition. The method further includes evaluating the complex alert expression to initiate display of at least one alert.

20 Claims, 6 Drawing Sheets

FIG. 4

SYSTEM, METHOD, AND SOFTWARE FOR AUTOMATING COMPLEX ALERTS

TECHNICAL FIELD

The present disclosure relates generally to alert management, and more particularly to a system, method, and software for automating complex alerts.

BACKGROUND

Patient monitoring systems include alert systems. For example, alert systems may identify simple alert conditions such as a blood pressure exceeding a certain threshold. Proprietary systems include interfaces to display alerts.

SUMMARY

According to the present disclosure, disadvantages and problems associated with previous techniques for alert management may be reduced or eliminated.

In certain embodiments, a method for automating complex alerts includes receiving, at a complex alert interface, first parameters and a first comparison operator. The first parameters and the first comparison operator are indicative of a first condition. The method further includes receiving, at the complex alert interface, second parameters and a second comparison operator. The second parameters and the second comparison operator are indicative of a second condition. The method further includes generating, at the complex alert interface, a complex alert expression based on a mathematical aggregate of the first condition and the second condition. The method further includes evaluating the complex alert expression to initiate display of at least one alert.

Certain embodiments of the present disclosure may provide one or more technical advantages. Conventional alert management systems include simple logic to detect alert conditions such as variables crossing thresholds. While many patient conditions may be detected by examining a combination of variables crossing thresholds, some patient conditions, such as sepsis, require complex logic to examine the number and type of variables. According to certain embodiments of the present disclosure, a complex alert interface addresses these challenges and facilitates a quick understanding of complex conditions such as the detection of sepsis. In one embodiment, the complex alert interface may be configured to detect one or more complex conditions. In one embodiment, the complex alert interface allows users to configure derived parameters and automated alerts that involve mathematical aggregate functions (count, sum) of the complex conditions. Thus, the possibilities for users, such as clinicians, to use alert systems, create derived parameters, identify complex medical conditions, and monitor patients may be expanded and the level of patient care improved.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

For a more complete understanding of the present disclosure and its features and advantages, reference is now made to the following description, taken in conjunction with the accompanying drawings, in which:

FIG. 4 illustrates one embodiment of an example display that may be generated by the mobile patient monitor of FIG. 2 to allow a user to configure a complex alert, according to certain embodiments of the present disclosure;

DESCRIPTION OF EXAMPLE EMBODIMENTS

Figure 1:
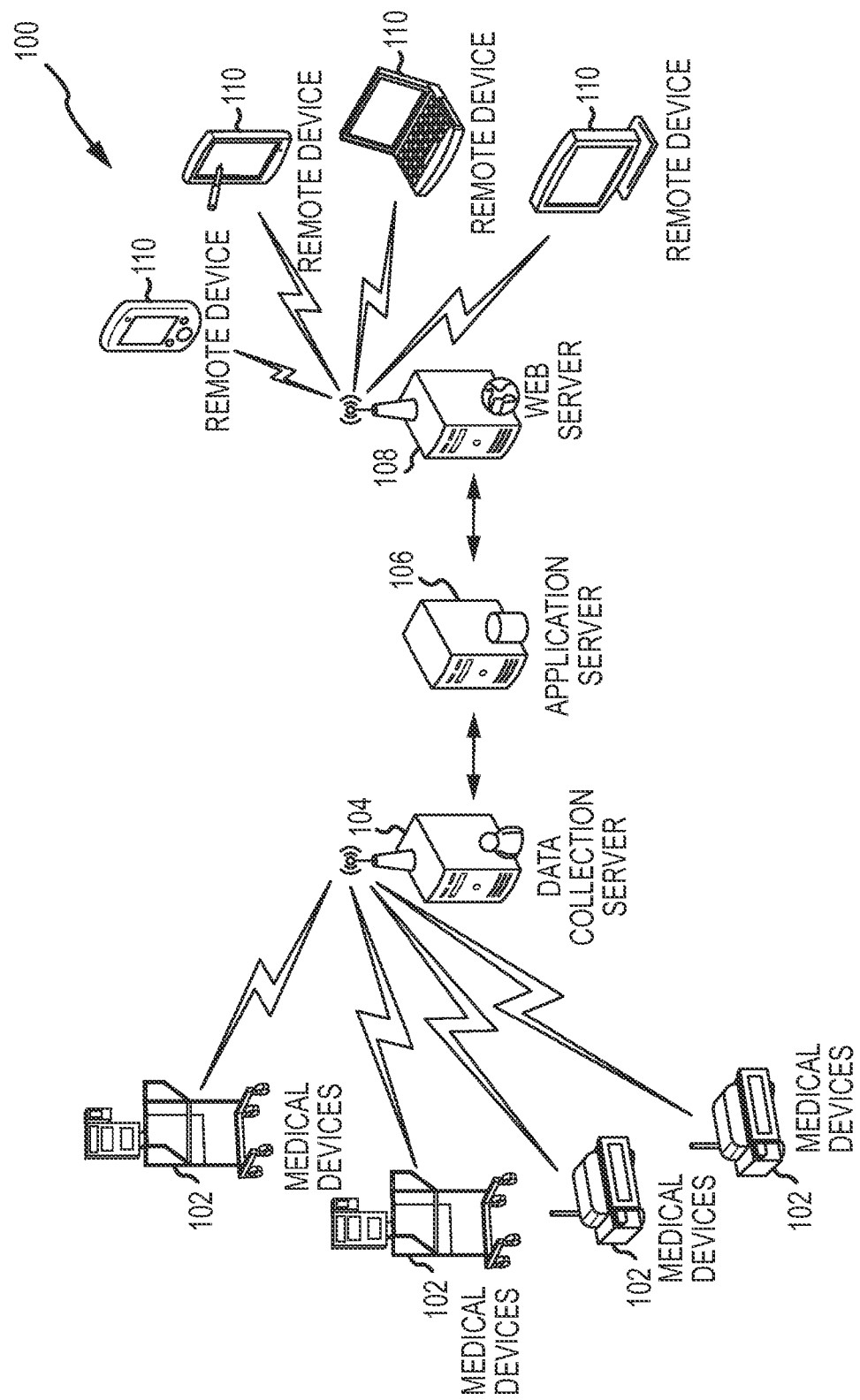
FIG. 1 illustrates an example system for automating complex alerts, according to certain embodiments of the present disclosure.

FIG. 1 illustrates an example system 100 for automating complex alerts, according to certain embodiments of the present disclosure. System 100 includes one or more medical devices 102, a data collection server 104, an application server 106, a web server 108, and one or more remote devices 110. According to one embodiment, system 100 is operable to monitor medical devices 102 and transform patient parameters into display parameters. In certain embodiments, medical devices 102 generate patient parameters or store patient parameters input by a user, such as a clinician. Patient parameters may refer to any patient identifiers, medical history, clinician notes, alarm thresholds, alarm events, device settings, measurements of values indicating physiological conditions such as oxygen saturation levels, pulse rates, heart rates, other vital signs, and any other output data from medical devices 102. Each medical device 102 may be connected to data collection server 104, which stores the patient parameters in a database. Application server 106 retrieves the patient parameters from the database and processes the patient parameters into display parameters for web server 108. Remote devices 110 request and receive the display parameters and display the display parameters through a browser, thereby enabling clinicians using the remote devices 110 to view the display parameters in remote locations. As described in more detail below, a complex alert interface includes complex logic to examine certain conditions and patient parameters to facilitate a quick identification of certain complex conditions at remote devices 110.

Although this particular implementation of system 100 is illustrated and primarily described, the present disclosure contemplates any suitable implementation of system 100 according to particular needs. For example, although this implementation of the complex alert interface is illustrated with remote devices 110 that may be using a web interface or a client/server interface, this disclosure contemplates any suitable implementation of the complex alert interface. In certain embodiments, alert notifications generated by the complex alert interface may be generated and displayed directly at medical devices 102 and all implementation details may be included in medical devices 102. In addition, a component of system 100 may include any suitable arrangement of elements, for example, an interface, logic, memory, other suitable element, or a combination of any of the preceding. An interface receives input, sends output, processes the input and/or output, performs other suitable operation, or performs a combination of any of the preceding. An interface may comprise hardware and/or software.

System 100 may include one or more medical devices 102. Medical devices 102 may be any devices that are used for tracking or treating patients. For example, medical devices 102 may include a ventilator connected to a patient to deliver respiratory therapy. As another example, medical devices 102 may include a pulse oximeter that monitors the oxygen saturation of a patient's blood. As another example, medical devices 102 may include a device for tracking a patient without monitoring physiological conditions. In short, medical devices 102 may include any suitable combination of software, firmware, and hardware used to support any medical function. It should be noted that any suitable number of medical devices 102 may be included in system 100. In addition, there may be multiple groups of medical devices 102 in system 100.

According to one embodiment, in addition to performing a medical function, medical devices 102 may generate output data tracked by medical devices 102. For example, the ventilator may generate entries indicating the average volume of air expelled in each breath. The ventilator may generate entries including the parameter settings used by the ventilator and an identification of whether any alarms have been triggered. The ventilator may store the generated entries in local memory and output the entries. In some embodiments, medical devices 102 may generate output data that is related to tracking patient identifications or locations, without necessarily generating data related to a physiological condition. In certain embodiments, medical devices 102 may output data in response to a data request. In certain other embodiments, medical devices 102 may constantly stream output data.

Medical devices 102 may be communicatively coupled to data collection server 104 via a network, according to one embodiment. The network facilitates wireless or wireline communication. The network may communicate, for example, IP packets, Frame Relay frames, Asynchronous Transfer Mode (ATM) cells, voice, video, data, and other suitable information between network addresses. The network may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, medical devices may be communicatively coupled to other suitable devices including data collection server 104, application server 106, web server 108, and remote devices 110.

System 100 may include one or more data collection servers 104, referred to primarily in the singular throughout this disclosure. Data collection server 104 may include one or more electronic computing devices operable to receive, transmit, process, and store data associated with system 100. For example, data collection server 104 may include one or more general-purpose PCs, Macintoshes, workstations, Unix-based computers, server computers, one or more server pools, or any other suitable devices. In certain embodiments, data collection server 104 includes a web server. In short, data collection server 104 may include any suitable combination of software, firmware, and hardware. Although a single data collection server 104 is illustrated, the present disclosure contemplates system 100 including any suitable number of data collection servers 104. Moreover, although referred to as a data collection server, the present disclosure contemplates data collection server 104 comprising any suitable type of processing device or devices.

According to one embodiment, data collection server 104 receives patient parameters from medical devices 102. For example, data collection server 104 may request patient parameters from a medical device 102 and receives patient parameter sets from the medical device 102 in response to the request. As another example, data collection server 104 may receive streamed output data from a medical device 102. As another example, data collection server 104 may be configured to periodically request new data from medical device 102. Data collection server 104 may map the received patient parameters to match internal fields in the database and then transmit the data to a database, according to one embodiment. The stored data may be accessed by application server 106.

System 100 may include one or more application servers 106, referred to primarily in the singular throughout this disclosure. Application server 106 may include one or more electronic computing devices operable to receive, transmit, process, and store data associated with system 100. For example, application server 106 may include one or more general-purpose PCs, Macintoshes, workstations, Unix-based computers, server computers, one or more server pools, or any other suitable devices. In short, application server 106 may include any suitable combination of software, firmware, and hardware. Although a single application server 106 is illustrated, the present disclosure contemplates system 100 including any suitable number of application servers 106. Moreover, although referred to as an application server, the present disclosure contemplates application server 106 comprising any suitable type of processing device or devices.

According to one embodiment, application server 106 creates a data service that runs on a conventional web services platform for transmitting data to web server 108. For example, application server 106 may create webpage data using the patient parameters, and that webpage data is transmitted to web server 108 for display. Application server 106 may maintain an activity log that logs data requests from remote devices 110 to track certain activities performed at the remote devices 110. Therefore, if a clinician selects a particular patient representation to zoom in and view ventilator data specific to that patient, that selection may trigger a data request that is logged by application server 106. When creating the webpage data, application server 106 may compare the current parameter settings of the ventilator, as indicated by entries in the patient parameter set, to prior parameter settings. If any changes are detected, application server 106 may flag those changes for presentation to users on remote devices 110. Specifically, application server 106 may create data causing the depiction of the changed patient parameters on the remote devices 110 to change color. Application server 106 may create additional data that causes a pop-up window to appear on the mobile device when any of the changed patient parameters are selected. That window may list all of the changed patient parameters and provides a single button through which a user may indicate that that the changed patient parameters have been viewed. If that button is activated, the mobile device may transmit a message to application server 106 and application server 106 may then unflag those patient parameters, such that the depiction of those patient parameters on remote device 110 may return to the original color. In certain embodiments, application server 106 may transmit data directly to remote devices 110.

System 100 may include one or more web servers 108, referred to primarily in the singular throughout this disclosure. Web server 108 may include one or more electronic computing devices operable to receive, transmit, process, and store data associated with system 100. For example, web server 108 may include one or more general-purpose PCs, Macintoshes, workstations, Unix-based computers, server computers, one or more server pools, or any other suitable devices. In short, web server 108 may include any suitable combination of software, firmware, and hardware. Although a single web server 108 is illustrated, the present disclosure contemplates system 100 including any suitable number of web servers 108. Moreover, although referred to as a web server, the present disclosure contemplates web server 108 comprising any suitable type of processing device or devices.

According to one embodiment, web server 108 creates a data service that runs on a conventional web services platform for receiving data from application server 106 and transmitting data to remote devices 110. For example, web server 108 may receive webpage data from application server 106 and transmitted, upon request in certain embodiments, to remote devices 110.

System 100 may include one or more remote devices 110. Remote devices 110 may be any device that provides output to and can receive input from a user, such as a clinician. Each remote device 110 may include one or more computer systems at one or more locations. Each computer system may include any appropriate input devices (such as a keypad, touch screen, mouse, or other device that can accept input), output devices, mass storage media, or other suitable components for receiving, processing, storing, and communicating data. Both the input device and output device may include fixed or removable storage media such as a magnetic computer disk, CD-ROM, or other suitable media to both receive input from and provide output to a user. Each computer system may include a personal computer, workstation, network computer, kiosk, wireless data port, personal data assistant (PDA), one or more processors within these or other devices, or any other suitable processing device.

According to one embodiment, remote devices 110 display one or more web pages hosted by application server 106 and/or web server 108 with patient parameters from medical devices 102. For example, a clinician may activate a browser on remote device 110 and navigate to the web page hosted by web server 108. The browser may render the web page, which includes patient parameters generated by medical devices 102. The web page may provide a summary of all the medical devices 102 under a clinician's responsibility. In addition, the web may display a detailed view that displays specific device data, therapy parameter data, and alarm status data.

Although FIG. 1 depicts separate devices for data collection server 104, application server 106, and web server 108, it will be readily apparent that the functions of these devices may be combined into a single device that receives patient parameters from medical devices 102 and transforms the patient parameters into display parameters. It will also be understood that this single device may alternatively transmit the display parameters to remote device 110.

It will also be understood that the functions may be allocated differently than shown, with application server 106 additionally performing the functions of web server 108 or the functions of data collection server 104. In another embodiment, a single device may receive patient parameters, transform those patient parameters into display parameters, and display the display parameters on a screen.

A user of system 100 may detect patient conditions by examining a combination of patient parameters crossing thresholds on remote device 110. However, some patient conditions require more complex logic to examine the number and type of variables. Thus, the user may be limited to examining only the patient parameters provided by medical devices 102, and therefore the user may not able to identify complex patient conditions.

In certain embodiments of the disclosure, system 100 may include a complex alert interface. The complex alert interface may refer to any suitable hardware and/or software operable to examine certain conditions, parameters, and/or operators and facilitate a quick identification of certain complex conditions at remote devices 110. Additional details of example embodiments of the complex alert interface are discussed below with reference to FIGS. 2-6.

Figure 2:
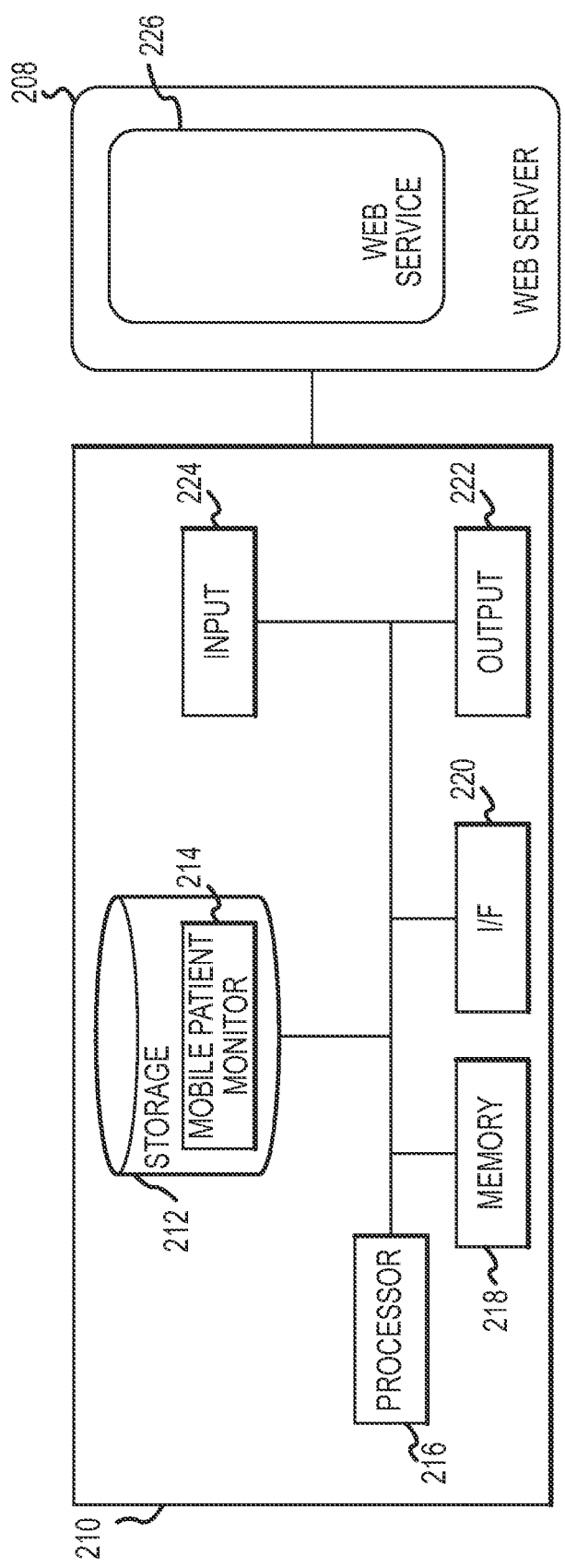
FIG. 2 illustrates an example remote device of the system for patient monitoring of FIG. 1, according to certain embodiments of the present disclosure.

FIG. 2 illustrates an example remote device 210 of the system 100 for patient monitoring in FIG. 1, according to certain embodiments of the present disclosure. Remote device 210 may be substantially similar to remote device 110 of FIG. 1. In FIG. 2, a remote device 210 is shown as a mobile telephone communicatively coupled with a web server 208 having a web service 226 capability. Web server 208 may be substantially similar to web server 108 of FIG. 1. Remote device 210 includes a storage device 212, a mobile patient monitor 214, a processor 216, a memory 218, a communication interface (I/F) 220, an output device 222, and an input device 224, which are discussed in further detail below. Although this particular implementation of remote device 210 is illustrated and primarily described, the present disclosure contemplates any suitable implementation of remote device 210 according to particular needs.

Storage device 212 may include any suitable device operable for storing data and instructions. Storage device 212 may include, for example, a magnetic disk, flash memory, optical disk, or other suitable data storage device.

Mobile patient monitor 214 may include any suitable logic embodied in computer-readable media, and when executed, that is operable to enable a user to communicate with web service 226 on web server 208 to view and manipulate data including display parameters. For example, mobile patient monitor 214 may include logic for receiving data from input device 224 and translating the data into a message to be sent to web service 226 on web server 208, in turn enabling a user to activate a browser and navigate a web page generated by web service 226 on web server 208 to view a complex alert interface. The complex alert interface may allow the user to examine certain conditions and facilitate a quick identification of certain complex conditions at remote device 210. The browser may provide, as part of the display parameters, a summary of all medical devices 102 associated with patients under a caregiver's responsibility, or a detailed view that displays specific medical device 102 configuration data, therapy parameter data, and alarm status data. Mobile patient monitor 214 may be configured to cause remote device 210 to request the most recent webpage data periodically from web service 226 on web server 208.

For example, when mobile patient monitor 214 requests a parameter (for example, by clicking a navigation link embedded in a display parameter), the browser transmits the request to web service 226. Web service 226 may extract the request and transmit a copy of the requested parameter in a display parameter format suitable for display by the browser, as well as any required formatting code, such as HTML code, for example. Examples of the browser may include a thick client such as an application, or a thin client browser such as Mozilla (Firefox), Netscape, Internet Explorer, or any future browsers.

Processor 216 may include any suitable device operable to execute instructions and manipulate data to perform operations for mobile patient monitor 214. Processor 216 may include, for example, any type of central processing unit (CPU).

Memory 218 may include any computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server). Memory 218 may comprise any other computer-readable tangible medium, or a combination of any of the preceding.

I/F 220 may include any suitable device operable to receive input for mobile patient monitor 214, send output from mobile patient monitor 214, perform suitable processing of the input or output or both, communicate to other devices, or any combination of the preceding. I/F 220 may include appropriate hardware (for example, a modem, network interface card, etc.) and software, including protocol conversion and data processing capabilities, to communicate through a LAN, WAN, or other communication system that allows mobile patient monitor 214 to communicate to other devices. I/F 220 may include one or more ports, conversion software, or a combination of any of the preceding.

Output device 222 may include any suitable device operable for displaying information to a user. Output device 222 may include, for example, a video display, a printer, a plotter, or other suitable output device.

Input device 224 may include any suitable device operable to input, select, and/or manipulate various data and information. Input device 224 may include, for example, a keyboard, mouse, graphics tablet, joystick, light pen, microphone, scanner, or other suitable input device.

Modifications, additions, or omissions may be made to remote device 210 without departing from the scope of the disclosure. The components of remote device 210 may be integrated or separated. Moreover, the operations of remote device 210 may be performed by more, fewer, or other components. For example, although mobile patient monitor 214 is displayed as part of storage device 212, mobile patient monitor 214 may be stored in any suitable location and the operations of mobile patient monitor 214 may be performed by more than one component. Additionally, operations of remote device 210 may be performed using any suitable logic. As used in this document, "each" refers to each member of a set or each member of a subset of a set. Further details of an example remote device 210 are provided below with reference to FIG. 3.

Figure 3:
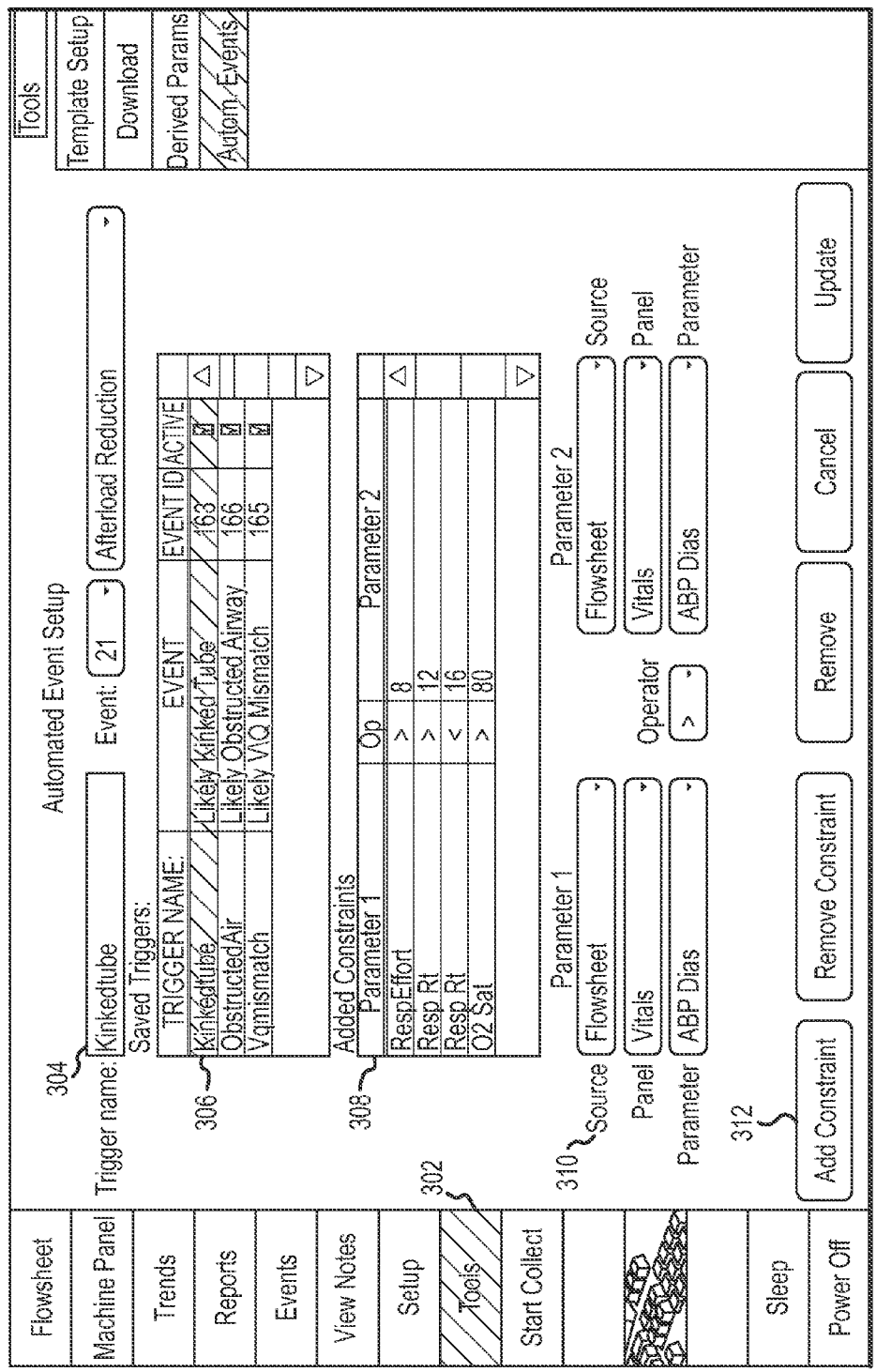
FIG. 3 illustrates one embodiment of an example display that may be generated by the mobile patient monitor of FIG. 2 to allow a user to configure a custom alert, according to certain embodiments of the present disclosure.

FIG. 3 illustrates one embodiment of an example display that may be generated by mobile patient monitor of FIG. 2 to allow a user to configure a custom alert, according to certain embodiments of the present disclosure. As shown in the illustrated embodiment, the display includes a window with an automated event setup area. The automated event setup area includes several buttons, including buttons 302 and 312, and several fields, including fields 304, 306, 308, and 310.

In certain embodiments, the display includes several menu tabs for managing alerts. In the illustrated embodiment, a left menu with a flowsheet tab, a machine panel tab, a trends tab, a reports tab, an events tab, a view notes tab, a setup tab, a tools tab, a start collect tab, a sleep tab, and a power off tab are displayed for a particular window and, as indicated by reference number 302, the tools tab is selected and an automated events tab is selected from the right menu. The automated event setup area includes several selectable buttons to add an alert to the mobile patient monitor. For example, button 312 may be selected to add a new constraint to a particular alert as described in more detail below.

In certain embodiments, a user may desire to configure a custom alert, such as Kinkedtube in field 304, and may add one or more constraints, such as the constraints in field 308, such that if all the constraints are satisfied then the custom alert will be triggered. In the illustrated embodiment, the Kinkedtube alert is considered a basic alert because it examines a combination of values crossing thresholds. Thus, the interface in the illustrated embodiment of FIG. 3 facilitates management of basic alerts. However, any alerts that require complex computations require a more advanced interface that is provided by the complex alert interface described in this disclosure and in more detail with reference to FIGS. 4-6.

Figure 4:
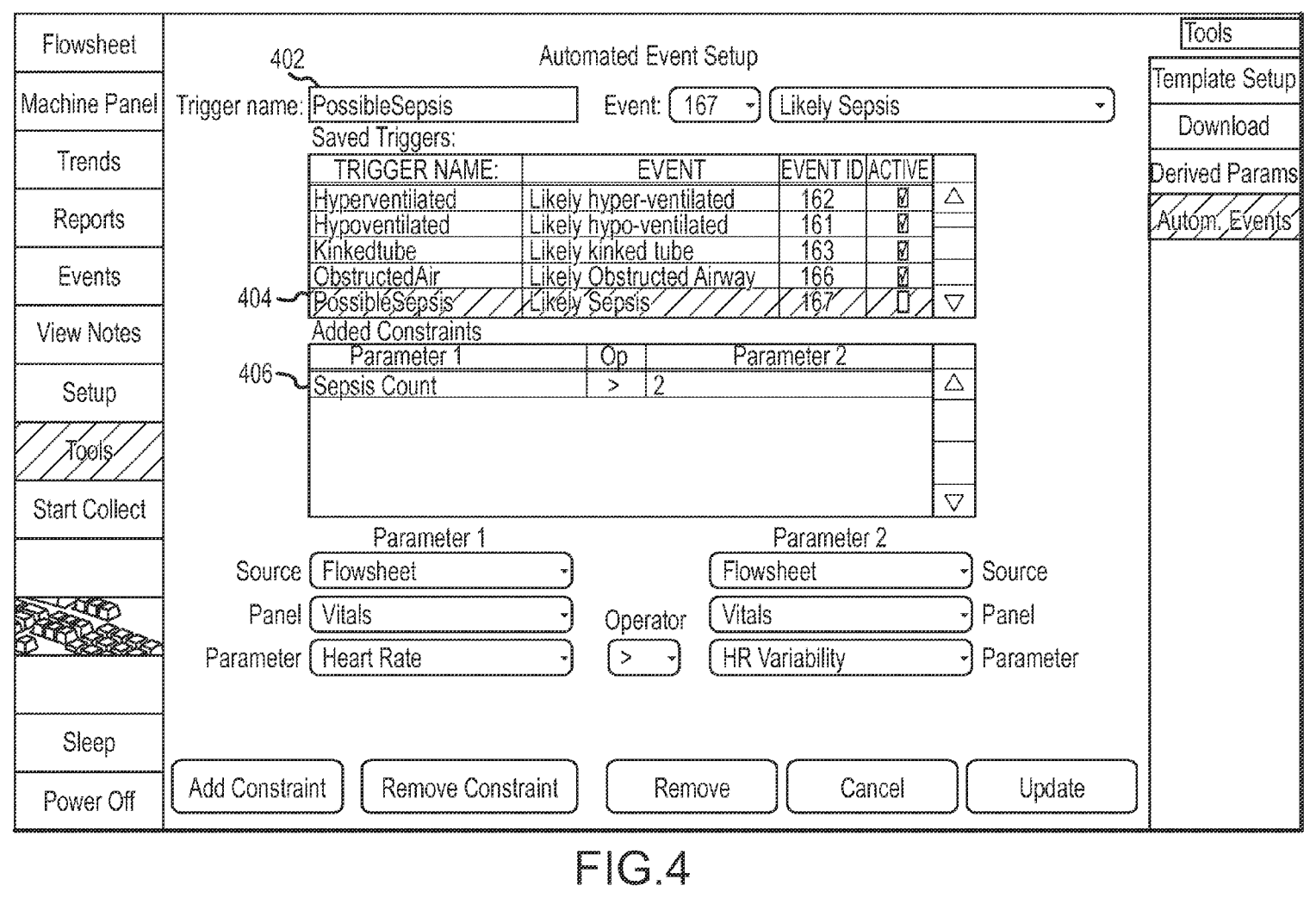
Figure 5:
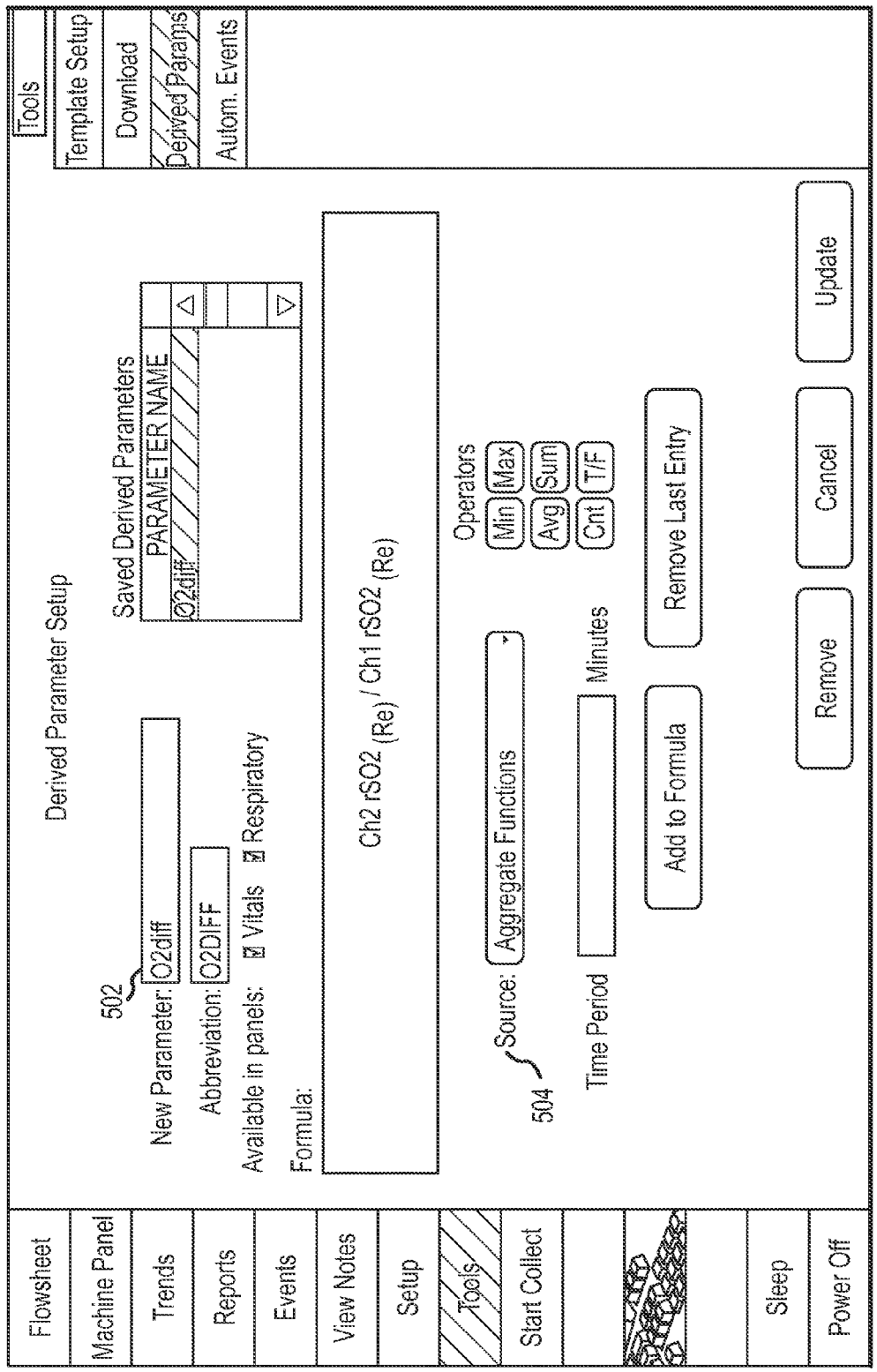
FIG. 5 illustrates one embodiment of an example display that may be generated by the mobile patient monitor of FIG. 2 to allow a user to configure a derived parameter for a complex alert, according to certain embodiments of the present disclosure.

FIGS. 4 and 5 illustrate one embodiment of example displays that may be generated by mobile patient monitor of FIG. 2 to allow a user to configure a complex alert, according to certain embodiments of the present disclosure. As described above with reference to FIG. 3, certain patient conditions may be detected by examining a combination of values crossing thresholds. However, some patient conditions require more complex logic to examine the number and type of variables. As described in more detail below, to facilitate detection of these more complex conditions, a complex alert interface allows an end user to configure automated complex alerts. For example, a user may configure derived parameters, such as the example as indicated by reference number 502 in FIG. 5, and automated complex alerts, such as the example indicated by reference number 406 in FIG. 4, that involve mathematical aggregate functions, such as a mathematical count of the number of satisfied conditions, and complex conditions, such as a logical OR operation between two parameters, according to one embodiment.

According to certain embodiments, the complex alert interface facilitates the generation of aggregate functions and complex conditions in automated physiologic data capture systems, such as the system described above in FIGS. 1 and 2, to facilitate identification of complex conditions, such as sepsis. At a complex alert interface, first patient parameters and a first comparison operator are received. The first patient parameters and the first comparison operator are indicative of a first condition. At the complex alert interface, second patient parameters and a second comparison operator are received. The second patient parameters and the second comparison operator are indicative of a second condition. A complex alert expression is generated based on a mathematical aggregate of at least the first condition and the second condition. According to one embodiment, the complex alert expression may refer to the following expression:

[FUNC]{(first parameter, comparison operator, (end first parameter or constant)) [or] (second parameter, comparison operator, (end second parameter or constant))}

As one example of a mathematical aggregate with complex conditions (also referred to as a complex alert expression in this disclosure) that includes a logical OR operation, the following expression may be generated at the complex alert interface for the detection of the early onset of sepsis:

Sepsis mathematical aggregate function: Count((Core Temperature>38 or Core Temperature<36) or Heart Rate>90 or (Respiration Rate>=20 or partial pressure of carbon dioxide (PaCO2)<32) or (white blood cells (WBC)<=4000 or WBC>=12000))>2

In this embodiment, if more than two of the thresholds are satisfied as indicated in the expression above and by reference number 406 in FIG. 4 (which is summed by the Count mathematical function), then the complex alert expression may initiate display of at least one alert that relates to sepsis. In certain other embodiments, the complex alert interface may detect one or more other complex disease states and may utilize other expressions. For example, pre-defined derived parameters may be configured that return 1 if the derived parameter evaluates as true, and return 0 if not true. As another example, a derived parameter may itself be a mathematical formula, as indicated by the O2Diff derived parameter indicated by reference number 502 in FIG. 5. In certain embodiments, the formula may include one or more subscripts that indicate the source of the value for the calculation. For example, in the illustrated embodiment, the formula Ch2rSO2(Re)/Ch1rSO2(Re) includes a subscript (Re) that indicates the source of the value for the calculation is a Regional Oximeter. As another example, the source of the value for the calculation may be a Cardio-Respiratory Monitor and may be indicated by the subscript (CR). Other sources may have other suitable subscripts.

In one embodiment, the complex alert interface may sum the evaluation of the derived parameters to evaluate the complex condition as follows:

Derived Parameter BadTemp: Count(Core Temperature>38 or Core Temperature<36)
Derived Parameter BadHeart: Count(Heart Rate)>90
Derived Parameter BadRR: Count((Respiration Rate>=20 or PaCO2<32)+1)/2
Derived Parameter BadWBC: Count(WBC<=4000 or WBC>=12000)

In this embodiment, each of the pre-defined derived parameters BadTemp, BadHeart, BadRR, and BadWBC are configured to return 1 if the derived parameter evaluates as true, and return 0 if not true. Therefore, one example of a mathematical aggregate function with complex conditions using the derived parameters described above for the detection of the early onset of sepsis may be generated as follows:

Sepsis mathematical aggregate function: Sum(BadTemp, BadHeart, BadRR, Bad WBC)>2

In this embodiment, if more than two of the derived parameters evaluate as true (e.g., their respective thresholds are satisfied and they return 1), then the complex alert expression may initiate display of at least one alert.

The complex alert interface may allow an end user to select at least a source for each parameter in an expression, a comparison operator (e.g., >, <, >=, <=, =, !=), and a constant, according to one embodiment. In certain embodiments, the parameters may be automatically captured parameters from medical devices or lab systems, manually input parameters, and parameters derived from automatically captured or manually input parameters.

In one embodiment of operation, patient parameters from medical devices 102 may be received and stored in one or more storage locations, such as data collection server 104, for evaluation by the complex alert interface. For example, patient parameters may be received in a raw format and may be parsed and semantically mapped to internal expressions. Once the patient parameters are received from medical devices 102 within a given time window, the complex alert interface may evaluate the patient parameters based on a complex alert expression to determine if any conditions match. Thus, one example embodiment of operation of the complex alert interface is as follows. First, patient parameters are received and stored from medical devices 102. Next, the patient parameters may be stored in a database and displayed on a beside display if appropriate. At the same time in this example embodiment, any derived parameters that are based on the stored patient parameters may be evaluated and stored in a database. Next, potentially at desired intervals, the complex alert interface may evaluate the patient parameters and/or derived parameters based on a complex alert expression to determine if any complex conditions are met. If complex conditions are met in this example embodiment, the matched alert expression may be stored in a database and display of at least one alert may be initiated on a remote device and/or a bedside display.

According to one embodiment, the complex alert interface does not require the development of new software for every complex disease state. Instead, the complex alert interface allows a clinician to modify the interface, including modifying the parameters and/or comparison operators, as the clinician sees fit.

Figure 6:
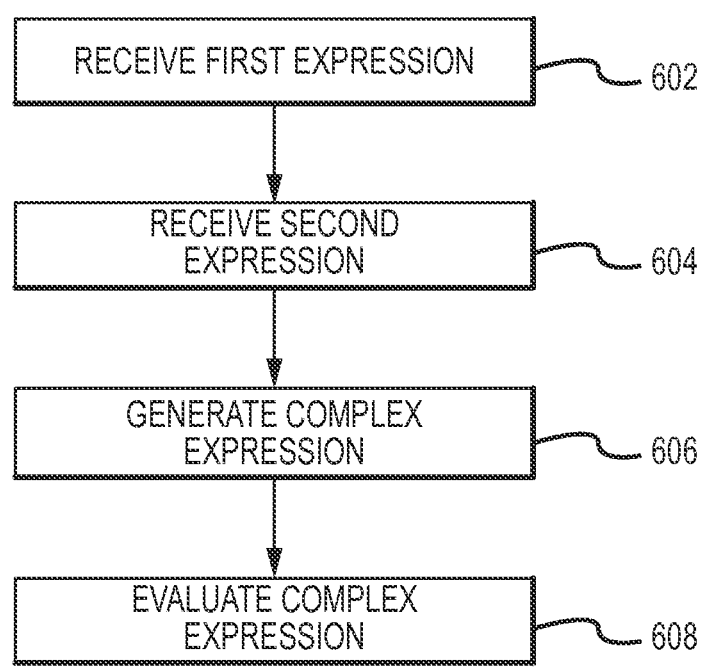
FIG. 6 illustrates an example method for automating complex alerts, according to certain embodiments of the present disclosure.

FIG. 6 illustrates an example method for automating complex alerts, according to certain embodiments of the present disclosure. The method begins at step 602 where first patient parameters and a first comparison operator are received at a complex alert interface. The first patient parameters and the first comparison operator are indicative of a first condition and may form a first expression. At step 604, second patient parameters and a second comparison operator are received at the complex alert interface. The second patient parameters and the second comparison operator are indicative of a second condition and may form a second expression. At step 606, a complex alert expression based on a mathematical aggregate of the first condition and the second condition is generated at the complex alert interface and may include the first expression and the second expression. At step 608, the complex alert expression evaluates the complex alert expression to initiate display of at least one alert. It should be understood that some of the steps illustrated in FIG. 6 may be combined, modified or deleted where appropriate, and additional steps may be added to the flowchart. Additionally, as indicated above, steps may be performed in any suitable order without departing from the scope of the disclosure.

Although the present disclosure has been described with several embodiments, diverse changes, substitutions, variations, alterations, and modifications may be suggested to one skilled in the art, and it is intended that the disclosure encompass all such changes, substitutions, variations, alterations, and modifications as fall within the spirit and scope of the appended claims.

What is claimed is:

1. A method for automating complex alerts, comprising:
receiving, at a complex alert interface, a first plurality of patient parameters and at least a first comparison operator, the first plurality of patient parameters and the first comparison operator indicative of a first condition;
receiving, at the complex alert interface, a second plurality of patient parameters and at least a second comparison operator, the second plurality of patient parameters and the second comparison operator indicative of a second condition;
generating, at the complex alert interface, a complex alert expression based on the first condition and the second condition;
evaluating the complex alert expression to compute a mathematical aggregate based on the complex alert expression, wherein the mathematical aggregate is a mathematical count of a number of satisfied conditions and complex conditions; and
determining whether to initiate display of at least one alert on a remote device based on the computed mathematical aggregate.

2. The method of claim 1, wherein the mathematical aggregate of the first condition and the second condition comprises a logical OR operation of the first condition and the second condition.

3. The method of claim 1, wherein the mathematical aggregate of the first condition and the second condition comprises a mathematical sum operation of the first condition and the second condition.

4. The method of claim 1, wherein the at least one alert comprises a sepsis alert.

5. The method of claim 1, further comprising receiving a third plurality and a fourth plurality of patient parameters, wherein each of the first plurality of patient parameters, second plurality of patient parameters, third plurality of patient parameters, and fourth plurality of patient parameters are received from a respective medical device, wherein the complex alert expression is further based on a third condition and a fourth condition.

6. The method of claim 1, wherein the second condition comprises a measurement of a heart rate higher than a threshold.

7. The method of claim 1, further comprising generating, at the complex alert interface, a plurality of parameter input fields comprising one or more areas, an area corresponding to a respective parameter of the first and second plurality of patient parameters.

8. A system for automating complex alerts, comprising one or more processing units operable to:
   receive, at a complex alert interface, a first plurality of patient parameters and at least a first comparison operator, the first plurality of patient parameters and the first comparison operator indicative of a first condition;
   receive, at the complex alert interface, a second plurality of patient parameters and at least a second comparison operator, the second plurality of patient parameters and the second comparison operator indicative of a second condition;
   generate, at the complex alert interface, a complex alert expression based on the first condition and the second condition;
   evaluate the complex alert expression to computer a mathematical aggregate based on the complex alert expression, wherein the mathematical aggregate is a mathematical count of a number of satisfied conditions and complex conditions; and
   determine whether to initiate display of at least one alert on a remote device based on the computed mathematical aggregate.

9. The system of claim 8, wherein the aggregate of the first condition and the second condition comprises a logical OR operation of the first condition and the second condition.

10. The system of claim 8, wherein the aggregate of the first condition and the second condition comprises a mathematical sum operation of the first condition and the second condition.

11. The system of claim 8, wherein the at least one alert comprises a sepsis alert.

12. The system of claim 8, wherein the one or more processing units are further operable to receive a third plurality and a fourth plurality of patient parameters, wherein each of the first plurality of patient parameters, second plurality of patient parameters, third plurality of patient parameters, and fourth plurality of patient parameters are received from a respective medical device, wherein the complex alert expression is further based on a third condition and a fourth condition.

13. The system of claim 8, wherein the second condition comprises a measurement of a heart rate higher than a threshold.

14. The system of claim 8, wherein the one or more processing units are operable to generate, at the complex alert interface, a plurality of parameter input fields comprising one or more areas, an area.

15. Software for automating complex alerts, the software embodied in a non-transitory computer-readable medium and when executed operable to:
   receive, at a complex alert interface, a first plurality of patient parameters and at least a first comparison operator, the first plurality of patient parameters and the first comparison operator indicative of a first condition;
   receive, at the complex alert interface, a second plurality of patient parameters and at least a second comparison operator, the second plurality of patient parameters and the second comparison operator indicative of a second condition;
   generate, at the complex alert interface, a complex alert expression based on the first condition and the second condition;
   evaluate the complex alert expression to compute a mathematical aggregate based on the complex alert expression, wherein the mathematical aggregate is a mathematical count of a number of satisfied conditions and complex conditions; and
   determine whether to initiate display of at least one alert on a remote device based on the computed mathematical aggregate.

16. The software of claim 15, wherein the aggregate of the first condition and the second condition comprises a logical OR operation of the first condition and the second condition.

17. The software of claim 15, wherein the aggregate of the first condition and the second condition comprises a mathematical sum operation of the first condition and the second condition.

18. The software of claim 15, wherein the at least one alert comprises a sepsis alert.

19. The software of claim 15, wherein the software is further operable to receive a third plurality and a fourth plurality of patient parameters, wherein each of the first plurality of patient parameters, second plurality of patient parameters, third plurality of patient parameters, and fourth plurality of patient parameters are received from a respective medical device, wherein the complex alert expression is further based on a third condition and a fourth condition.

20. The software of claim 15, wherein the second condition comprises a measurement of a heart rate higher than a threshold.

* * * * *